United States Patent [19]

Zaitsu et al.

[11] Patent Number: 4,827,144
[45] Date of Patent: May 2, 1989

[54] PARTICLE DETECTING DEVICE WITH PARTICLE SCANNING

[75] Inventors: Yasushi Zaitsu; Fumio Toyama, both of Kanagawa, Japan

[73] Assignee: Fuji Electric Co., Ltd., Kanagawa, Japan

[21] Appl. No.: 126,632

[22] Filed: Nov. 30, 1987

[51] Int. Cl.$^4$ ............................................. G01N 15/06
[52] U.S. Cl. ...................................... 250/574; 356/336
[58] Field of Search ...................... 350/3.71; 377/11; 250/573, 574; 356/335, 336

[56] References Cited

U.S. PATENT DOCUMENTS

| | | | |
|---|---|---|---|
| 3,133,445 | 5/1964 | Richard | 377/11 |
| 3,676,647 | 7/1972 | Statton et al. | 377/11 |
| 4,094,583 | 6/1978 | Kondo et al. | 350/358 |
| 4,701,005 | 10/1987 | Nosuchi | 350/6.71 |

Primary Examiner—David C. Nelms
Attorney, Agent, or Firm—Finnegan, Henderson, Farabow, Garrett, & Dunner

[57] ABSTRACT

A particle detecting device for detecting particles contained in a flowing sample fluid is provided which comprises a light beam irradiating mechanism for irradiating the sample fluid with a light beam, the light beam irradiating mechanism including a light beam deflecting portion for directing the light beam across the flow of the sample fluid and for causing the light beam to scan a predetermined irradiation region of the sample fluid, this scanning causing a portion of the light beam to be scattered by the particles in the irradiation region to produce scattered light; a light receiving mechanism for receiving the scattered light and for converting the scattered light to an electrical signal; and a signal processor coupled to the light receiving mechanism for processing the electric signal to obtain at least one of the number of particles in the sample fluid and a particle size distribution for the particles in the sample fluid. The electrical signal includes a series of pulse groups, each of the pulse groups comprising a plurality of pulses. Accordingly, the signal processor detects the peak value of the pulses of at least one of the pulse groups and/or detects the number of pulse groups.

9 Claims, 5 Drawing Sheets

PARTICLE DETECTING DEVICE WITH PARTICLE SCANNING

BACKGROUND OF THE INVENTION

1. Field of the Invention

This invention relates to a particle detecting device used for counting the number of low-density particles in a flowing fluid and measuring the corresponding particle size distribution by irradiating the fluid containing the particles with a focused light beam and detecting scattered light of the light beam reflected by each particle.

2. Description of the Related Art

A particle detecting device that detects particles such as dust or cells is useful in processes for preparing semiconductors and pharmaceuticals, for example, in measuring the cleanliness of the atmosphere, the quality of purified water and medicines, etc. In medical sciences and biology, such a device is useful for testing the condition of cells. Recently, there has been a need for a particle detecting device which is capable of detecting fine particles.

Figure 8:
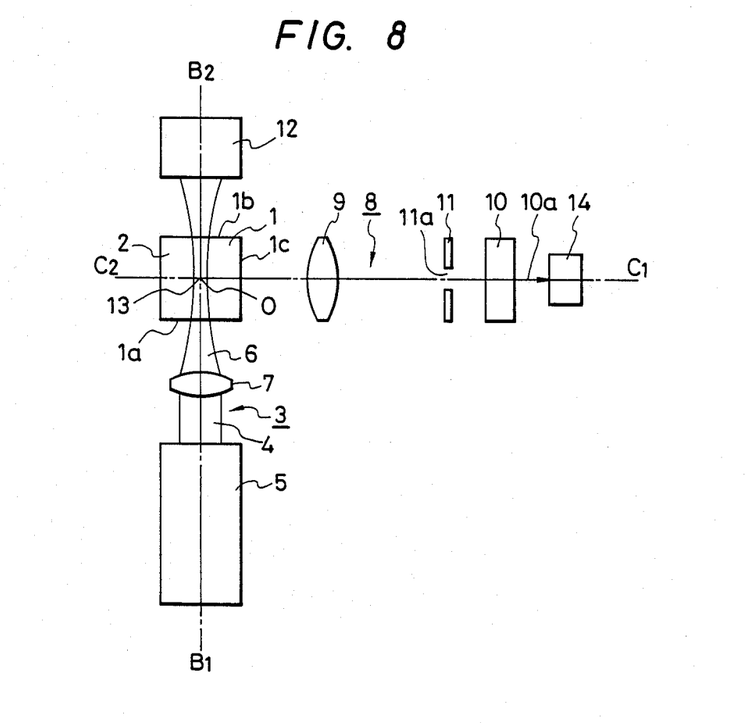
FIG. 8 is a schematic diagram of a conventional particle detecting device.

FIG. 8 illustrates the structure of a conventional device for detecting particles in a fluid. Referring to FIG. 8, reference numeral 1 represents a flow-cell having a square cross-sectional shape and transparent side walls 1a, 1b and 1c. A sample fluid 2 containing the particles to be measured flows through flow-cell 1 in a direction perpendicular to the drawing sheet, i.e., out of the page.

Reference numeral 3 represents a light beam irradiating mechanism comprising an irradiator 5 which irradiates a plurality of parallel rays as a pencil beam 4 and a focusing lens 7 which focuses pencil beam 4 to form a light beam 6. Light beam irradiating mechanism 3 is adapted to irradiate sample fluid 2 in flow-cell 1 with light beam 6 through transparent side wall 1a of flow-cell 1.

Figure 9:
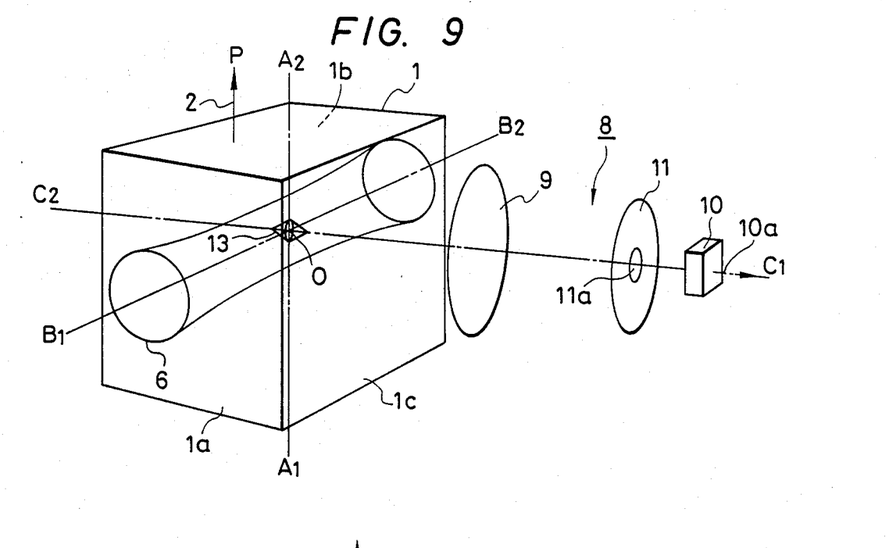
FIG. 9 is an enlarged perspective view of selected principal components of the device shown in FIG. 8.

For convenience of illustration and shown particularly in FIG. 9, a rectilinear coordinate system is used here having coordinate axes $A_1$-$A_2$, $B_1$-$B_2$, and $C_1$-$C_2$ which intersect at an origin O. Origin O is located in the center of flow-cell 1. Axes $B_1$-$B_2$ and $C_1$-$C_2$ define a plane parallel to the sheet of paper on which FIG. 8 is drawn. Axis $A_1$-$A_2$ passes through the origin perpendicular to the plane defined by axes $B_1$-$B_2$ and $C_1$-$C_2$. During irradiation of flow-cell 1 with light beam 6, the optical axis of light beam 6 is aligned with axis $B_1$-$B_2$.

A portion of light beam 6 is scattered by the particles in sample fluid 2 in the vicinity of origin O when sample fluid 2 is irradiated by light beam 6. Reference numeral 8 represents a light receiving mechanism for receiving this scattered light. Light receiving mechanism 8 comprises a condensing lens 9 which condenses the scattered light, and a photoelectric converter 10 which converts the light condensed by lens 9 into an electrical signal 10a corresponding to the quantity of scattered light and outputs electrical signal 10a. Light receiving mechanism 8 further comprises an aperture member 11 having a circular aperture 11a for restricting the angle of the scattered light incident upon photoelectric converter 10. Aperture member 11 is disposed between condensing lens 9 and photoelectric converter 10. The optical axis of light receiving mechanism 8 is aligned with axis $C_1$-$C_2$.

Reference numeral 12 represents a beam block capable of absorbing light beam 6 to prevent portions of light beam 6 which have penetrated into flow-cell 1 as stray light from entering into light receiving mechanism 8.

Reference numeral 14 represents a signal processing portion of light receiving mechanism 8 which processes electrical signal 10a to indicate the state of the particles in sample fluid 2, for example, the number of particles and the particle size distribution.

The operation of light receiving mechanism 8 of the particle detecting device shown in FIG. 8 will now be described with reference to FIG. 9, which provides an enlarged perspective view of principal components of the particle detecting device shown in FIG. 8. The rectilinear coordinate system described above is shown in FIG. 9 to comprise axes $A_1$-$A_2$, $B_1$-$B_2$, and $C_1$-$C_2$, each intersecting at origin O and being mutually perpendicular. Axis $A_1$-$A_2$ is aligned with the longitudinal axis of flow-cell 1. Reference character P represents an arrow which shows the direction of flow of sample fluid 2, the arrow P paralleling axis $A_1$-$A_2$. Reference numeral 13 represents a cubic visual field of light receiving mechanism 8, which field is disposed in the vicinity of origin O. Visual field 13 is formed in a spindle shape, its axis being aligned with axis $C_1$-$C_2$ and its center being at origin O. Light receiving mechanism 8 is as described above. Only the light irradiated by visual field 13 and captured by light receiving mechanism 8 is photoelectrically converted by light receiving mechanism 8 since visual field 13 is arranged within the visual field of light receiving mechanism 8. Referring to FIG. 9, the structure of the device as described above causes the entire portion of visual field 13 to be included in light beam 6. Scattered light in the form of light pulses is produced when the particles conveyed by sample fluid 2 pass through visual field 13. The scattered light pulses impinge upon photoelectric converter 10 and are photoelectrically converted into electrical signal 10a, which also takes the form of pulses. As a result, the number and size of the particles which pass through visual field 13 can be detected from the number and size of pulses in signal 10a. Signal processing portion 14 of light receiving mechanism 8 as shown in FIG. 8 is adapted to process signal 10a as described above.

In the process of detecting the particles as shown and described above, if the quantity of light received by light receiving mechanism 8 is insufficient, it is impossible to accurately detect the particles. Therefore, in general, the luminous intensity of the scattered light can be increased by narrowing the width of light beam 6 to increase the quantity of scattered light. In general, the diameter of light beam 6 in the vicinity of origin O is designed to be several tens of micrometers to several hundreds of micrometers. Focusing lens 7 shown in FIG. 8 is provided for this reason.

Figure 10A:
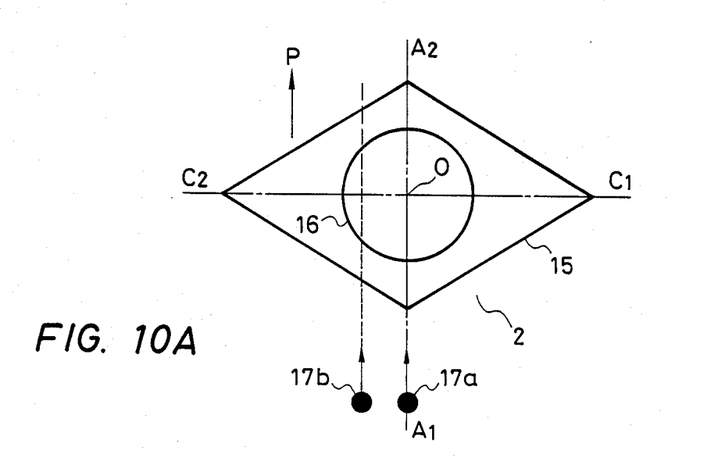
FIG. 10A is a diagram of a visual field of the device shown in FIG. 8 which illustrates the disposition of a light beam.
Figure 10B:
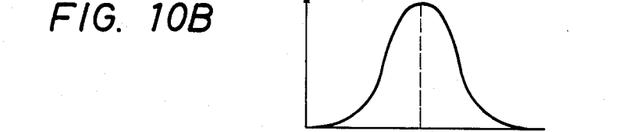
FIG. 10B is a graph showing the luminous intensity distribution of the light beam.

In the process of detecting the number and size of particles which pass visual field 13 as shown in FIGS. 8 and 9, if the distribution of the luminous intensity of light beam 6 is nonuniform in visual field 13, errors in detection will occur as will now be described. FIG. 10 is a diagram illustrating why errors in detection occur. FIG. 10A is a cross-sectional view of visual field 13 obtained by cutting through the portion of flow-cell 1 in the vicinity of visual field 13 as shown in FIG. 9 by the plane defined by axes $A_1$-$A_2$ and $C_1$-$C_2$. Reference numerals 15 and 16 respectively represent the visual field and light beam which correspond to visual field 13 and light beam 6 shown in FIG. 9. In this state, light beam 16 penetrates visual field 15. Reference numerals 17a and 17b represent two spherical particles having the same diameter which cross visual field 15 in the direction P as they are conveyed by sample fluid 2. With reference to FIG. 10A, when particles 17a and 17b move as described above, if the luminous intensity of light beam 16 has a spindle-shaped distribution with the maximum value of the luminous intensity at origin O as shown in FIG. 10B, the scattering of light from light beam 16 may not always occur in correspondence with the route of particles 17a and 17b passing through visual field 15. Furthermore, even if particles 17a and 17b are the same size, scattered light of differing luminous intensities may be produced. In the former case, an error in detecting the number of particles will occur, while in the latter case an error in detecting the size of the particles will occur. Since particle detecting devices as described above typically employ a laser beam as the light beam so that the size of even the smallest particles can be detected by increasing the luminous intensity of this light beam as it irradiates the sample fluid, such a laser beam usually has a bell-shaped luminous intensity distribution as shown in FIG. 10B and, consequently, errors in detection such as those described above may occur.

Therefore, a method is typically employed in which the flow channel of the sample fluid is narrowed to restrict fluid flow to the vicinity of axis $A_1$-$A_2$ (FIG. 10A) wherein the luminous intensity is distributed uniformly, as shown by the luminous intensity curve of FIG. 10B. Alternatively and with reference to FIG. 9, a method is employed in which visual field 13 is disposed in the portion of flow-cell 1 in which the luminous intensity of light beam 6 is distributed substantially uniformly. Particle detecting devices employing the former method are unsatisfactory in that, if the luminous intensity of the light beam is increased by narrowing the beam width to enable the device to detect relatively smaller particles, the nonuniformity of the luminous intensity distribution in the sample fluid increases. As a result, the degree of error in detecting particle sizes increases or, in other words, the particle size resolving power of the detecting device deteriorates. When the flow field of the sample fluid is narrowed to restrict the sample fluid to the portion of flow-cell 1 in which the luminous intensity of the light beam has a uniform distribution, deterioration of resolving power can be avoided by reducing the quantity of fluid that can be measured in a predetermined time, e.g., by reducing the flow rate.

In detecting devices employing the latter method, when light beam 6 is narrowed to enable the device to detect smaller particles, the particle size resolving power of the device deteriorioates for reasons similar to those described above. The luminous intensity is not distributed uniformly where visual field 13 of light receiving mechanism 8 is disposed in substantially the entire region of light beam 6. To prevent this deterioration of resolving power, aperture 11a of aperture member 11 can be reduced in size to narrow visual field 13, thus reducing the quantity of light capable of passing through aperture 11a. As a result, the quantity of scattered light impinging upon photoelectric converter 10 may not increase even though the luminous intensity of light beam 6 is increased. Thus, the device cannot be adapted in this fashion to detect relatively smaller particles.

SUMMARY OF THE INVENTION

Accordingly, it is an object of the present invention to provide a particle detecting device capable of overcoming drawbacks of conventional particle detecting devices such as those discussed above, and in which relatively smaller particles are detectable without decreasing the flow rate of the sample fluid containing the particles and without deteriorating the particle size resolving power of the device.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

To achieve the foregoing objects, and in accordance with the purposes of the invention as embodied and broadly described here, a particle detecting device is provided which comprises light beam irradiating means for irradiating the sample fluid with a light beam, the light beam irradiating means including light beam deflecting means for directing the light beam across the flow of the sample fluid and for causing the light beam to scan a predetermined irradiation region of the sample fluid, the scanning causing a portion of the light beam to be scattered by the particles in the irradiation region to produce scattered light; light receiving means for receiving the scattered light and for converting the scattered light to an electrical signal; and signal processing means coupled to the light receiving means for processing the electrical signal to obtain at least one of the number of particles in the sample fluid and a particle size distribution for the particles in the sample fluid.

The electrical signal may include a series of pulse groups, each of the pulse groups comprising a plurality of pulses. Accordingly, the signal processing means is adapted to detect the peak value of the pulses of at least one of said pulse groups and the number of pulse groups.

Particle detecting devices according to the present invention have the capacity to substantially expand the size in the beam-scanning direction of a region wherein the luminous intensity of the light beam irradiating the measured sample fluid is uniformly distributed. Furthermore, satisfactory particle size resolving power of such particle detecting devices can be achieved regardless of the luminous intensity distribution of the light beam. Therefore, particle detecting devices in accordance with the invention can measure particles of reduced size without decreasing the flow rate of the sample fluid and without deteriorating the particle size resolving power.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention. Of the drawings.

DESCRIPTION OF THE PREFERRED EMBODIMENTS

Reference will now be made in detail to the presently preferred embodiments of the invention as illustrated in the accompanying drawings, in which like reference characters designate like or corresponding parts throughout the several drawings.

Figure 1:
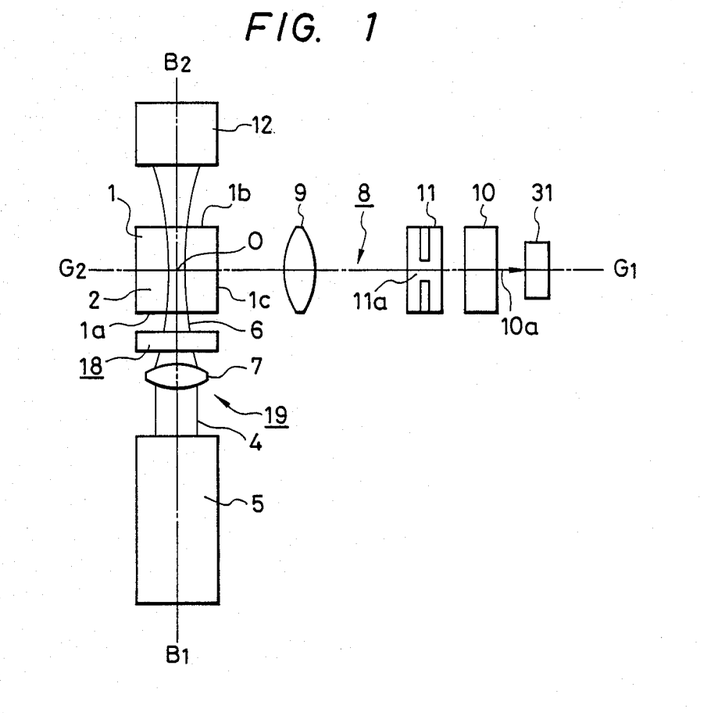
FIG. 1 is a schematic diagram of a first preferred embodiment of the present invention.

FIG. 1 is a schematic diagram of a particle detecting device in accordance with a first embodiment of the present invention. The general structure of the first preferred embodiment is similar to that of the conventional device described above, as can be seen by comparing FIGS. 1 and 8. There are two major differences, however, between the embodiment shown in FIG. 1 and the conventional particle detecting device shown in FIG. 8. The first preferred embodiment (FIG. 1) includes a light beam deflecting portion 18 between focusing lens 7 and flow-cell 1 for repeatedly scanning sample fluid 2 with light beam 6, light beam 6 being a straight beam. The first preferred embodiment also includes a signal processing portion 31 for performing signal processing in a manner different from that of signal processing portion 14 shown in FIG. 8.

Reference numeral 19 represents a light beam irradiating mechanism comprising irradiator 5, focusing lens 7, and light beam deflecting portion 18. Preferably, irradiator 5 includes a He-Ne laser generator which irradiates a laser beam in the form of a pencil beam 4 comprising a plurality of parallel rays. Light beam deflecting portion 18 of the first preferred embodiment is constructed as shown in FIG. 2, which shows selected critical components of the embodiment of FIG. 1.

Figure 2:
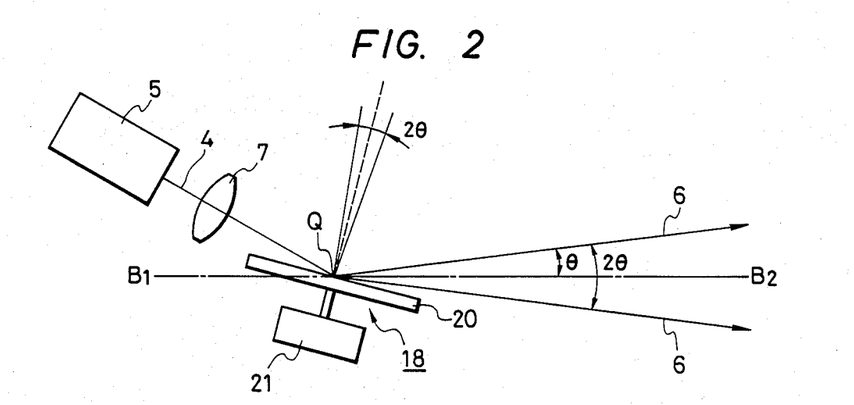
FIG. 2 is a diagram of selected principal components of the embodiment shown in FIG. 1.

In FIG. 2, reference numeral 20 represents a movable reflecting mirror the inclination of which is adapted to repeatedly or periodically change its angular position, i.e., oscillate, with respect to pencil beam 4 over a range of, for example, 20° in response to the vibrating magnetic field of an electromagnet 21 while pencil beam 4 is incident upon a point Q on a reflective surface of mirror 20. Reflecting mirror 20 and electromagnet 21 thus cause light beam 6 irradiated from the light beam deflecting portion 18 to oscillate correspondingly, as illustrated in FIG. 2, e.g., over an angular range of 20°. Therefore, the preferred embodiment of FIG. 1 scans sample fluid 2 with light beam 6, whose direction oscillates in a straightforward manner as described above.

The plane within sample fluid 2 to be scanned, which passes through point Q and includes light beam 6 as it oscillates relative to point Q, is parallel to the plane of the paper on which FIG. 1 is drawn. As can be clearly seen from FIG. 2, light beam 6 is deflected by angle $\theta$ on each side of axis $B_1$-$B_2$, i.e., over a total range of $2\theta$ or 20°.

Figure 3A:
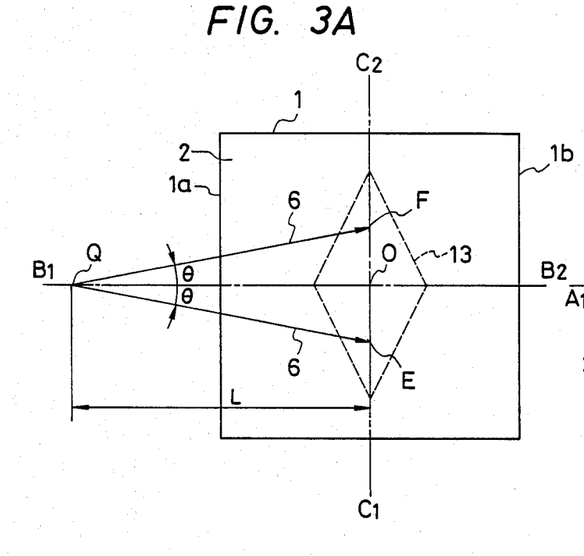
FIG. 3A is a plan view of the flow-cell shown in FIG. 1
Figure 3B:
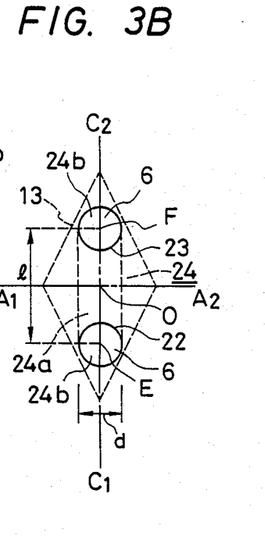
FIG. 3B is a side view of the same flow-cell.

FIG. 3 is a diagram illustrating the operation of the embodiment shown in FIGS. 1 and 2, wherein FIG. 3A is a plan view of flow-cell 1 taken along the plane defined by axes $B_1$-$B_2$ and $C_1$-$C_2$ and, thus, parallel to the plane of the paper on which FIG. 1 apears, and FIG. 3B is a side view of the visual field 13 taken along the plane defined by axes $A_1$-$A_2$ and $C_1$-$C_2$ and perpendicular to the plane of the paper on which FIG. 1 appears, as in FIG. 10A. As described above, light beam 6 is deflected in an oscillatory manner by mirror 20 from point Q to various locations along axis $C_1$-$C_2$ between two extreme positions on axis $C_1$-$C_2$ corresponding to the maximum angular deflection of mirror 20. When light beam 6 is deflected by mirror 20 to its respective maximum outward positions or extremes, the optical axis of light beam 6 passes through corresponding points E and F on axis $C_1$-$C_2$, which creates circular spots 22 and 23, respectively, on the plane formed by axes $A_1$-$A_2$ and $C_1$-$C_2$, these spots corresponding to the light intensity distribution of light beam 6, as shown in FIG. 3B.

In FIG. 3, reference character L represents the distance between point Q on mirror 20 and origin O of the rectlinear coordinate system within flow-cube 1. Reference character l denotes the distance between points E and F. Reference character d denotes the diameter of circular spots 22 and 23 formed by light beam 6.

The oscillatory deflection of light beam 6 over an angular range of 20° causes an irradiation region 24 to be periodically and repeatedly irradiated with light beam 6. Irradiation region 24 lies in the plane formed by axes $A_1$-$A_2$ and $C_1$-$C_2$ and its size and shape are defined by a rectangular band-shaped portion 24a having length l and width d and semicircular portions 24b which extend continuously from rectangular band-shaped portion 24a. In other words, irradiation region 24 is the region irradiated by light beam 6 as it oscillates. In this case, visual field 13 includes irradiation region 24. Since irradiation region 24 and visual field 13 are arranged as shown in FIG. 3, electrical signal 10a as shown in FIG. 4 is output from photoelectric converter 10 (FIG. 1) in accordance with the light scattered by the particles passing through irradiation region 24.

Figure 4:
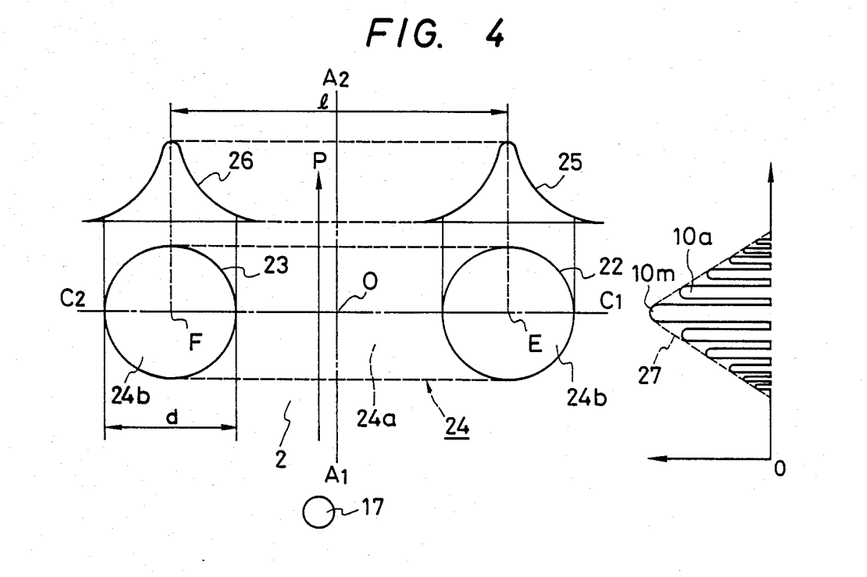
FIG. 4 is a view illustrating the operation of the embodiment shown in FIGS. 1 and 2 wherein the position of the light beam in the view field is shown and compared with a graph scattered light intensity similar to FIG. 3B.

FIG. 4 is a view of irradiation region 24 as shown in FIG. 3B but in which visual field 13 is omitted for the convenience of explanation. In FIG. 4, reference numeral 17 represents a particle moving through and crossing irradiation region 24 at a uniform velocity in the direction P parallel to axis $A_1$-$A_2$. Reference numeral 25 represents a curve of luminous intensity distribution characteristics for beam spot 22 along axis $C_1$-$C_2$. Reference numeral 26 represents a curve of luminous intensity distribution characteristics for beam spot 23 which corresponds to the luminous intensity distribution characteristics curve 25. Luminous intensity distribution curves 25 and 26 both have a bell-shaped configuration. As a result, the luminous intensity distribution of light beam 6 reaches a maximum at the portion of axis $C_1$-$C_2$ between points E and F in irradiation region 24. The device is configured so that l is greater than d. Since the deflection speed of light beam 6 is considerably faster than the relative speed of particle 17, electrical signal 10a which comprises a serial pulse train or a series of pulse groups is generated in accordance with the light scattered by particles such as particle 17 crossing irradiation region 24, as shown in FIG. 4. An envelope 27 connecting the peaks of the pulses of signal 10a (shown as a dashed line in FIG. 4) is bell-shaped and corresponds to luminous intensity distribution characteristics curves 25 and 26. The number of particles crossing irradiation region 24 can thus be detected by counting the number of pulse groups or pulse trains in electrical signal 10a having this envelope shape. The size of the particles can be detected by measuring the peak value 10m of electrical signal 10a which corresponds to each of the particles. The signal processing portion 31 shown in FIG. 1 is adapted to process electrical signal 10a in the manner described above.

In the embodiment shown in FIG. 1, for example, if d is set at 0.1 mm and the oscillation frequency of light beam 6 is set at 20 KHz, the time necessary for particle 17 moving at a speed of 50 mm/s to pass through irradiation region 24 is $0.1/50 = 2 \times 10^{-3}$ s. Accordingly, the number of pulses forming envelope 27 is 80. As can be clearly seen from the explanation above, the greater the number of pulses forming envelope 27, the more closely the shape of envelope 27 resembles characteristics curves 25 and 26. Thus, the particle size resolving power is significantly improved when measuring the size of particles using this device. However, if the number of pulses is insufficient, the particle size resolving power deteriorates because the probability of irradiating the particles at the peak portion of characteristics curves 25 or 26 becomes too low.

Since the particle detecting device shown in FIG. 1 can detect particles in the manner described above, the shape of luminous intensity distribution characteristics curves 25 and 26 of light beam 6 shown in FIG. 4 does not affect the particle size resolving power of the device. In the device of FIG. 1, the portion of sample fluid 2 in which the luminous intensity of light beam 6 is distributed uniformly is increased in the direction of the scanning of light beam 6 relative to conventional devices as described above, as can be clearly seen by comparing FIG. 4 with FIG. 10. Therefore, in a particle detecting device in accordance with the first preferred embodiment of the invention, if the portion of sample fluid 2 in which the luminous intensity is distributed uniformly is restricted by narrowing light beam 6 to increase the capacity of the device to detect smaller particle sizes, the particle size resolving power does not deteriorate. Furthermore, the width of deflection θ of light beam 6 can be set independently of the luminous intensity of light beam 6 in such a device. Therefore, narrowing of light beam 6 to enable the device to detect relatively smaller particles does not require narrowing the flow passage of sample fluid 2 for devices in which the flow passage of sample fluid 2 is set to cross irradiation region 24, as shown in FIG. 4. That is, the particle detecting device shown in FIG. 1 can be employed to detect very small particles without any need to decrease the flow rate of sample fluid 2 and without deteriorating the particle size resolving power of the device.

Figures 5, 6:
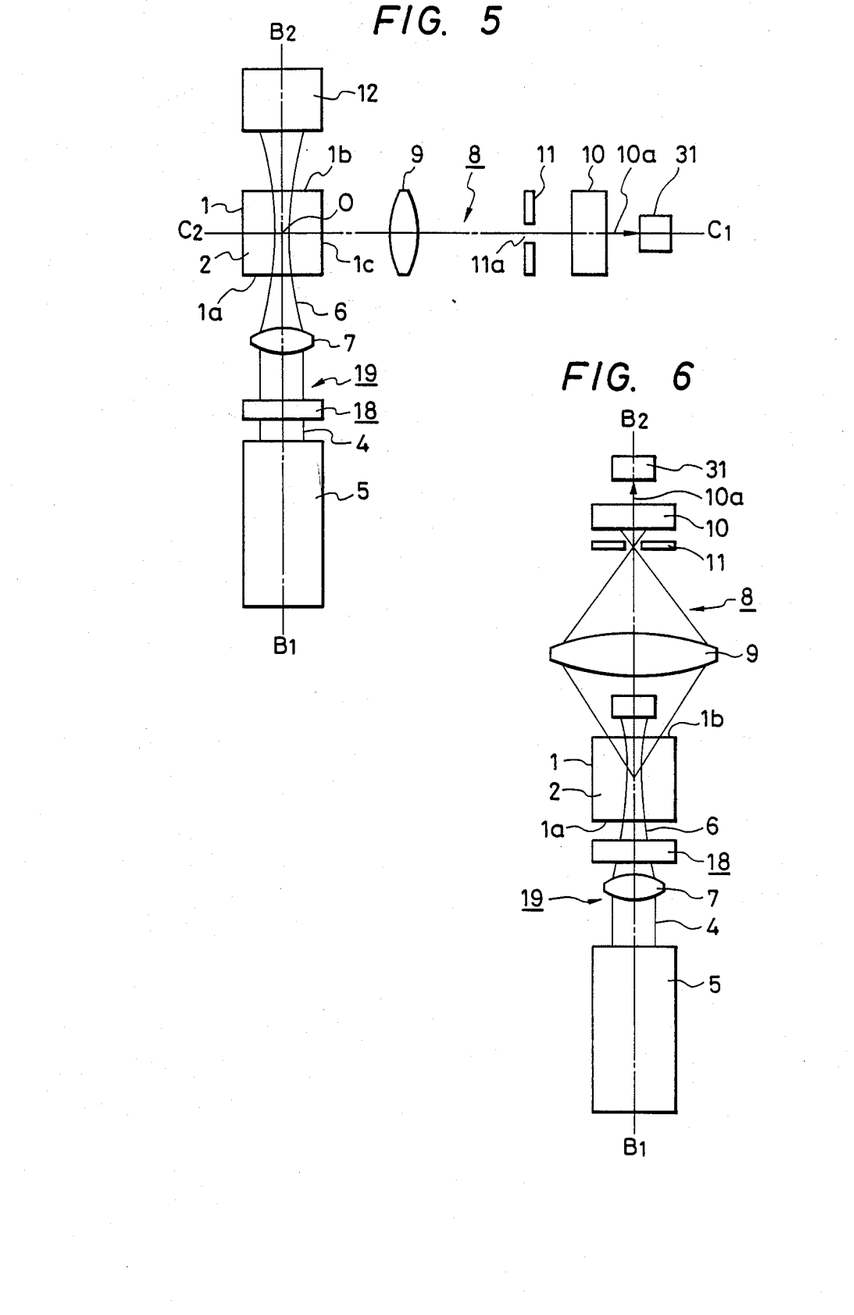
FIG. 5 is a schematic diagram of a second preferred embodiment of the invention.
FIG. 6 is a schematic diagram of a third preferred embodiment of the invention.

A second embodiment of the present invention is shown in FIG. 5. The device of FIG. 5 differs from the device of FIG. 1 in that the relative positions of focusing lens 7 and light beam deflecting portion 18 are reversed. It will be apparent to those with ordinary skill in the art that particles can be detected using the device of FIG. 5 in a similar manner and with similar effect to the manner and effect obtainable using the device shown in FIG. 1. However, since lens 7 in the embodiment of FIG. 5 is disposed adjacent to flow-cell 1, a lens having a short-focal length can be employed as lens 7. Since the numerical aperture of lens 7 can therefore be enlarged, light beam 6 can be tightly focused, thus enabling the particle detecting device shown in FIG. 5 to detect very small particles.

A third embodiment of the present invention is shown in FIG. 6. The device shown in FIG. 6 differs from the device of FIG. 1 in that light receiving mechanism 8 is arranged to receive the forward scattered light of light beam 6 from flow-cell 1. It will be apparent to those of ordinary skill in the art that the device of FIG. 6 can detect particles in a similar manner and with similar effect to the manner and effect obtainable using the device of FIG. 1. In particular, the particle detecting device shown in FIG. 6 provides the advantage that the detection of particles is facilitated because the luminous intensity of the forward scattered light is stronger than light scattered sideways, as in the aforesaid embodiments.

Figure 7:
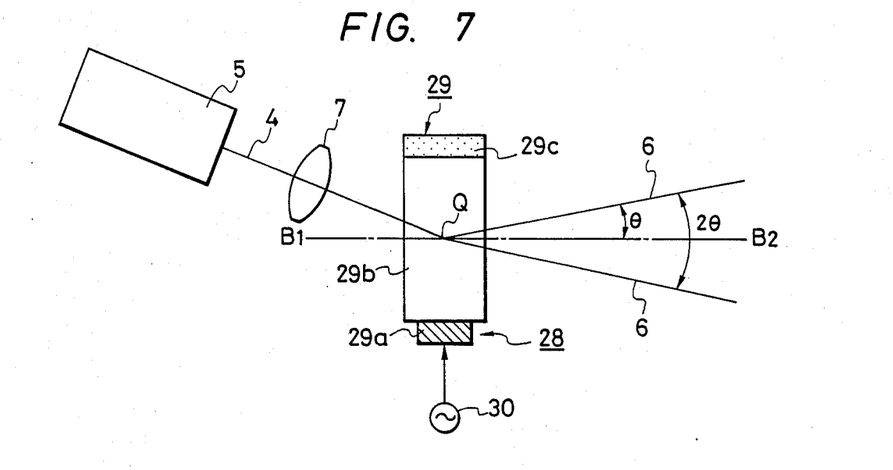
FIG. 7 is a diagram of an alternative light beam deflecting portion to the light beam deflecting portion shown in FIG. 2.

FIG. 7 is a diagram of a light beam deflecting portion 28 which may be employed as an alternative to the light beam deflecting portion 18 shown in FIG. 2. Referring to FIG. 7, reference numeral 29 represents a photoacoustic deflecting elemental device which includes an ultrasonic oscillator 29a, a photo-acoustic medium 29b, and a sound absorbing material 29c. Ultrasonic oscillator 29a is operated by a power source 30. Photo-acoustic medium 29b functions in part to transmit ultrasonic waves irradiated from ultrasonic oscillator 29a. Photo-acoustic medium 29b also functions to deflect the direction of the light beam which is incident upon it in accordance with the conditions of the ultrasonic wave being transmitted through photo-acoustic medium 29b. Sound absorbing material 29c absorbs ultrasonic waves which have been transmitted through photo-acoustic medium 29b. Light beam deflecting portion 28 includes photo-acoustic deflecting elemental device 29 and power source 30. Since light beam deflecting portion 28 is capable of converting the incident pencil beam 4 into light beam 6 which vibrates or oscillates at high speed over an angular range of, for example, 20° in response to power source 30, light beam deflecting portion 28 can be employed as an alternative to light beam deflecting portion 18 of the aforementioned embodiments of the particle detecting device.

It will be understood that the particle detecting device of the present invention is not limited to the preferred embodiments described here. For example, although aperture 11a in aperture member 11 has a circular shape in the aforementioned embodiments, it can also be formed into a slit or other shape. The optical axis of light receiving mechanism 8 may intersect the optical axis of light beam 6 at an angle that is different from that employed in the aforementioned embodiments. Light beam 6 as projected onto sample fluid 2 is not limited to a circular cross-section. The cross-sectional shape of flow-cell 1 and the spatial directions of the three axes $A_1$-$A_2$, $B_1$-$B_2$, and $C_1$-$C_2$ are not limited to those shown in the aforementioned embodiments. The particle detecting device according to the present invention is also capable of measuring the flow velocity of a fluid containing particles by counting the number of pulses in the electric signal 10a shown in FIG. 4.

The preferred embodiments of the invention as described above provide the advantage over similar devices in the prior art that the region in which the luminous intensity of light beam 6 irradiating sample fluid 2 is distributed uniformly can be substantially lengthed in the scanning direction of light beam 6 so that the luminous intensity distribution of light beam 6 does not affect the particle size resolving power of the particle detecting device. Consequently, the particle detecting devices of the preferred embodiments are capable of detecting relatively smaller particles without reducing the flow rate of sample fluid 2 and without deteriorating the particle size resolving power of the devices.

Additional advantages and modifications will readily occur to those skilled in the art. Therefore, the invention in its broader aspects is not limited to the specific details, representative devices, and illustrative examples shown and described. Accordingly, departures may be made from such details without departing from the spirit or scope of the general inventive concept as defined by the appended claims and their equivalents.

What is claimed is:

1. A particle detecting device for detecting particles contained in a flowing sample fluid, said device comprising:
    light beam irradiating means for irradiating the sample fluid with a light beam, said light beam irradiating means including light beam deflecting means for directing said light beam across the flow of the sample fluid and for causing said light beam to repeatedly scan a predetermined irradiation region of the sample fluid, said scanning causing a portion of said light beam to be scattered by the particles in said irradiation region to produce scattered light;
    light receiving means for receiving said scattered light and for converting said scattered light to an electrical signal, said electrical signal including a series of pulse groups, each of said pulse groups comprising a plurality of pulses; and
    signal processing means coupled to said light receiving means for processing said electrical signal, said signal processing means detecting the peak value of the pulses of at least one of said pulse groups and detecting the number of said pulse groups, to thereby obtain at least one of the number of particles in the sample fluid and a particle size distribution for the particles in the sample fluid.

2. A particle detecting device as recited in claim 1, wherein said light beam deflecting means includes a movable mirror for directing said light beam to said irradiation region, and drive means for mechanically oscillating said mirror to scan said light beam in said irradiation region.

3. A particle detecting device as recited in claim 2, wherein said drive means includes an oscillating magnetic field source for producing an oscillating magnetic field in the vicinity of said mirror, said oscillating magnetic field causing said mirror to mechanically oscillate and scan said light beam in said irradiation region.

4. A particle detecting device as recited in claim 1, wherein said light beam deflecting means includes a photo-acoustic medium through which said light beam is directed prior to irradiating the sample fluid, and an ultrasonic oscillator for producing ultrasonic waves having variable properties in said photo-acoustic medium, said ultrasonic oscillator causing the properties of said ultrasonic waves to selectively vary to correspondingly deflect said light beam.

5. A particle detecting device as recited in claim 1, wherein said light receiving means includes an aperture member having an aperture for selectively providing said scattered light to said light receiving means.

6. A particle detecting device as recited in claim 1, wherein said light receiving means is positioned to receive said scattered light scattered from said irradiation region at an angle that is substantially perpendicular to said light beam.

7. A particle detecting device as recited in claim 1, wherein said light receiving means is positioned to receive said scattered light scattered from said irradiation region at an angle that is substantially parallel to said light beam.

8. A particle detecting device as recited in claim 1, including focusing means for focusing said light beam prior to deflecting said light beam with said light beam deflecting means.

9. A particle detecting device as recited in claim 1, including focusing means for focusing said light beam after deflecting said light beam with said light beam deflecting means.

* * * * *